United States Patent
Kusleika et al.

(10) Patent No.: US 9,011,478 B2
(45) Date of Patent: Apr. 21, 2015

(54) EMBOLIC FILTERS WITH A DISTAL LOOP OR NO LOOP

(75) Inventors: Richard S. Kusleika, Eden Prairie, MN (US); John C. Oslund, Blaine, MN (US)

(73) Assignee: Covidien LP, Mansfield, MA (US)

( * ) Notice: Subject to any disclaimer, the term of this patent is extended or adjusted under 35 U.S.C. 154(b) by 1747 days.

(21) Appl. No.: 11/374,943

(22) Filed: Mar. 14, 2006

(65) Prior Publication Data

US 2006/0167490 A1 Jul. 27, 2006

Related U.S. Application Data

(63) Continuation of application No. 10/354,831, filed on Jan. 30, 2003, now abandoned.

(51) Int. Cl.
*A61M 29/00* (2006.01)
*A61F 2/01* (2006.01)

(52) U.S. Cl.
CPC ........... *A61F 2/013* (2013.01); *A61F 2002/011* (2013.01); *A61F 2002/015* (2013.01); *A61F 2002/018* (2013.01); *A61F 2230/0008* (2013.01); *A61F 2230/0067* (2013.01)

(58) Field of Classification Search
CPC ..... A61F 2/01; A61F 2/013; A61F 2002/011; A61F 2002/015; A61F 2002/016; A61F 2002/018
USPC ................... 606/113, 127, 200, 191; 128/831
See application file for complete search history.

(56) References Cited

U.S. PATENT DOCUMENTS 4,425,908 A * 1/1984 Simon .......................... 606/200
4,619,246 A 10/1986 Molgaard-Nielsen et al.
(Continued)

FOREIGN PATENT DOCUMENTS

EP 0 350 043 A1 1/1990
EP 0 350 043 B1 1/1990
(Continued)

OTHER PUBLICATIONS

Nitinol Technical Specifications: Transformation, Physical, Electrical, Magnetic and Mechanical Properties. Johnson Matthey Medical Components. Accessed Jun. 11, 2013 at <<http://jmmedical.com/resources/221/Nitinol-Technical-Properties.html>>.*
(Continued)

*Primary Examiner* — Julian W Woo
*Assistant Examiner* — Shaun L David
(74) *Attorney, Agent, or Firm* — Alana T. Bergman, Esq.

(57) ABSTRACT

The invention provides a device for filtering emboli from blood flowing through a lumen defined by the walls of a vessel in a patient's body, comprising a filter element and a self-expanding radial element associated with the filter element. The filter element is expandable from a collapsed configuration when the filter element is restrained to an expanded configuration when the filter element is unrestrained. The filter element comprises a self-expanding material having pores. The filter element has proximal and distal portions and a central portion, and has a shape in the expanded configuration which defines a cavity having a proximal facing opening. The self-expanding radial element is distal of the filter element, and the self-expanding radial element is adapted to maintain the filter element centered in the lumen.

22 Claims, 4 Drawing Sheets

(56) References Cited

U.S. PATENT DOCUMENTS

| | | | |
|---|---|---|---|
| 4,643,184 A * | 2/1987 | Mobin-Uddin | 606/200 |
| 5,662,671 A | 9/1997 | Barbut et al. | |
| 5,709,704 A * | 1/1998 | Nott et al. | 606/200 |
| 5,814,064 A | 9/1998 | Daniel et al. | |
| 5,919,224 A | 7/1999 | Thompson et al. | |
| 5,941,896 A * | 8/1999 | Kerr | 606/200 |
| 6,001,118 A | 12/1999 | Daniel et al. | |
| 6,019,784 A | 2/2000 | Hines | |
| 6,053,932 A | 4/2000 | Daniel et al. | |
| 6,059,814 A | 5/2000 | Ladd | |
| 6,066,149 A | 5/2000 | Samson et al. | |
| 6,123,715 A | 9/2000 | Amplatz | |
| 6,129,739 A | 10/2000 | Khosravi | |
| 6,179,859 B1 * | 1/2001 | Bates et al. | 606/200 |
| 6,179,861 B1 | 1/2001 | Khosravi et al. | |
| 6,203,732 B1 | 3/2001 | Clubb et al. | |
| 6,206,868 B1 | 3/2001 | Parodi | |
| 6,231,589 B1 * | 5/2001 | Wessman et al. | 606/200 |
| 6,245,089 B1 | 6/2001 | Daniel et al. | |
| 6,277,139 B1 | 8/2001 | Levinson et al. | |
| 6,312,407 B1 | 11/2001 | Zadno-Azizi et al. | |
| 6,325,815 B1 | 12/2001 | Kusleika et al. | |
| 6,336,934 B1 | 1/2002 | Gilson et al. | |
| 6,346,116 B1 | 2/2002 | Brooks et al. | |
| 6,361,545 B1 | 3/2002 | Macoviak et al. | |
| 6,364,895 B1 | 4/2002 | Greenhalgh | |
| 6,368,339 B1 | 4/2002 | Amplatz | |
| 6,383,171 B1 | 5/2002 | Gifford et al. | |
| 6,383,196 B1 | 5/2002 | Leslie et al. | |
| 6,391,044 B1 | 5/2002 | Yadav et al. | |
| 6,425,909 B1 | 7/2002 | Dieck et al. | |
| 6,461,370 B1 | 10/2002 | Gray et al. | |
| 6,485,501 B1 | 11/2002 | Green | |
| 6,494,907 B1 | 12/2002 | Bulver | |
| 6,610,077 B1 | 8/2003 | Hancock et al. | |
| 6,893,451 B2 | 5/2005 | Cano et al. | |
| 6,964,672 B2 | 11/2005 | Brady et al. | |
| 2001/0012951 A1 * | 8/2001 | Bates et al. | 606/200 |
| 2002/0004667 A1 | 1/2002 | Adams et al. | |
| 2002/0022858 A1 * | 2/2002 | Demond et al. | 606/200 |
| 2002/0042627 A1 | 4/2002 | Brady et al. | |
| 2002/0045916 A1 | 4/2002 | Gray et al. | |
| 2002/0055747 A1 | 5/2002 | Cano et al. | |
| 2002/0058911 A1 | 5/2002 | Gilson et al. | |
| 2002/0058964 A1 | 5/2002 | Addis | |
| 2002/0091409 A1 | 7/2002 | Sutton et al. | |
| 2002/0107541 A1 | 8/2002 | Vale et al. | |
| 2002/0111648 A1 | 8/2002 | Kusleika et al. | |
| 2002/0128680 A1 | 9/2002 | Pavlovic | |
| 2002/0161394 A1 | 10/2002 | Macoviak et al. | |
| 2002/0165576 A1 | 11/2002 | Boyle et al. | |
| 2002/0188314 A1 | 12/2002 | Anderson et al. | |
| 2003/0023264 A1 | 1/2003 | Dieck et al. | |
| 2003/0040771 A1 | 2/2003 | Hyodoh et al. | |
| 2004/0111111 A1 | 6/2004 | Lin | |

FOREIGN PATENT DOCUMENTS

| | | |
|---|---|---|
| EP | 1 181 900 A2 | 2/2002 |
| EP | 1 226 795 A2 | 7/2002 |
| WO | WO 94/06372 | 3/1994 |
| WO | WO 96/01591 | 1/1996 |
| WO | WO 97/25002 | 7/1997 |
| WO | WO 98/38920 | 9/1998 |
| WO | WO 98/39053 | 9/1998 |
| WO | WO 99/16382 | 4/1999 |
| WO | WO 00/16705 | 3/2000 |
| WO | WO 00/53119 | 9/2000 |
| WO | WO 00/53120 | 9/2000 |
| WO | WO 00/58964 | 10/2000 |
| WO | WO 00/67670 | 11/2000 |
| WO | WO 01/08595 A1 | 2/2001 |
| WO | WO 01/15629 A1 | 3/2001 |
| WO | WO 01/21100 A1 | 3/2001 |
| WO | WO 01/89413 A2 | 11/2001 |
| WO | WO 02/43595 A2 | 6/2002 |
| WO | WO 02/054988 A2 | 7/2002 |
| WO | WO 02/094111 A2 | 11/2002 |
| WO | WO 2004/052239 A2 | 6/2004 |

OTHER PUBLICATIONS

US 6,348,062, 2/2002, Hopkins et al. (withdrawn).
US 6,461,371, 10/2002, McInnes (withdrawn).
U.S. Appl. No. 09/628,212, filed Feb. 28, 2000, John C. Oslund et al. (Ref. No. 19369/103/101).
U.S. Appl. No. 10/093,572, filed Mar. 8, 2002, Richard S. Kusleika et al. (Ref. No. MVA1003US).
U.S. Appl. No. 10/132,562, filed Apr. 25, 2002, Kent D. Anderson et al. (Ref. No. MVA1005US).
U.S. Appl. No. 10/354,679, filed Jan. 30, 2003, Thomas L. Clubb et al. (Ref. No. EV31001US).
U.S. Appl. No. 10/354,829, filed Jan. 30, 2003, Richard S. Kusleika et al. (Ref. No. EV31002US).
U.S. Appl. No. 10/096,624, filed Mar. 12, 2002, Marwane Berrada et al. (Ref. No. 16848.133.1.1).
Search Report for International Application No. PCT/US2004/002756 (3 pages).
Search Report for International Application No. PCT/US2004/002587.
Search Report for Counterpart International Application No. PCT/US2004/002757.
Sep. 30, 2009 European Search Report for Application No. EP 09009276.8 (6 pages).

* cited by examiner

*Fig. 1A*

(PRIOR ART)

*Fig. 1B*

(PRIOR ART)

EMBOLIC FILTERS WITH A DISTAL LOOP OR NO LOOP

This application is a continuation of U.S. application Ser. No. 10/354,831, filed Jan. 30, 2003 now abandoned, the contents of which are incorporated by reference herein.

FIELD OF THE INVENTION

This invention relates to devices used in a blood vessel or other lumen in a patient's body. In particular, the present invention relates to devices for capturing emboli and particulate in a lumen.

BACKGROUND OF THE INVENTION

During vascular surgery or endovascular treatment of vessels including thrombectomy, atherectomy, balloon angioplasty, and/or stent deployment, debris such as plaque and blood clots can move from the treatment site through a vein or artery and compromise the flow of blood at a location removed from the treatment site. In particular, various protection systems have been developed to prevent such debris from embolizing in the vessel. Distal protection devices include filters and occlusive devices (e.g., balloons) placed distally of the treatment site. Proximal protection devices include filters and occlusive devices placed proximally of the treatment site. In the case of filters, emboli collect within or on the filter. The filter with captured emboli is typically collapsed into a recovery catheter and the catheter withdrawn from the patient's body.

In prior art filters it has been found that incorrect radial position of the filter within a body conduit can compromise the performance of the filter. Specifically, if a portion of the filter abuts a vessel wall, then the area of the filter available for performing the filtering function is reduced. Further, radial motion of an elongate member can cause the filter to lose wall apposition and thereby defeat the intended embolic capture function of the filter.

Most filters are mounted onto elongate support members, and the filters are comparatively flexible as compared to the elongate support members to which they are mounted. Radial motion of the elongate support member is often a consequence of back and forth axial motion of the elongate support member in tortuous body conduits. Radial motion of the elongate support member can compress the filter, causing it to lose apposition to the conduit wall and thereby defeat the intended embolic capture function. Control of elongate member radial position by use of proximal loops is discussed in U.S. Ser. No. 09/628,212, filed Jul. 28, 2000, entitled "Improved Distal Protection Device" and U.S. Ser. No. 10/093,572, filed Mar. 8, 2002, entitled "Distal Protection Devices Having Controllable Wire Motion," the contents of each of which are hereby incorporated by reference herein. Radial motion of the elongate support member can also press the filter against a conduit and reduce the area available for filtering emboli.

A need in the art remains for an embolic protection filter in which an elongate support member does not cause the filter to have excessive contact with a body conduit, thereby decreasing the filter area available for performing the filtering function.

SUMMARY OF THE INVENTION

The invention provides an embolic protection filter in which an elongate support member does not cause the filter to have excessive contact with a body conduit, thereby decreasing the filter area available for performing the filtering function. The invention also provides an embolic protection filter in which radial wire motion does not compromise filter wall apposition It is to be understood that both the foregoing general description and the following detailed description are exemplary and explanatory and are intended to provide further explanation of the invention as claimed.

DETAILED DESCRIPTION OF THE PREFERRED EMBODIMENTS

The terms "distal" and "proximal" as used herein refer to the relative position of the elongate support member, catheters, and filter in a lumen. Thus, "proximal" refers to a location upstream from the "distal" position. That is, the flow of a body fluid, such as blood, moves from the proximal to the distal portions of the device.

The invention encompasses the use of any filtration device to be deployed in a lumen or vessel of a patient. Although the examples relate generally to filter protection devices deployed distal to a treatment site, the device can also be deployed proximal to a treatment site in connection with interrupting or reversing flow through the vessel. In the case of a proximally deployed device, it will be advantageous to construct the device on a hollow elongate member so as to preserve access to the treatment site through the hollow member.

In a preferred embodiment, the distal protection system comprises a catheter which is loaded with an elongate support member or guidewire about which is disposed a distal protection filter. The elongate support member is structurally similar to a traditional guidewire in some respects. However, it is not used as a means of navigating the patient's vascular system and, therefore, does not need to be provided with all of the features of flexibility and steerability as does a traditional guidewire. With these differences in mind, the terms elongate support member and guidewire may be used interchangeably herein. A floppy tip (described further below) may be at the distal end of the elongate support member or guidewire. Typically, the filter is introduced into a blood vessel through an introducing catheter. Methods of introducing guidewires and catheters and the methods for the removal of such devices from vessels are well known in the art of endovascular procedures. In a typical procedure using the device of this invention, the elongate support member and filter are loaded into an introducing sheath or catheter and moved into the vessel and through the catheter to the treatment site. Typically, this is done by advancing a first, or introduction guidewire, through the vessel to the region of interest. A catheter is advanced over the guidewire to the region of interest, and the guidewire removed. Then the filter or other functional device carried by the elongate support member is advanced down a catheter sheath to the region of interest but within the catheter. The catheter sheath is withdrawn to deploy (expand) the filter at the region of interest. Alternatively, the filter is preloaded into a catheter and held in place by an outer sheath of the catheter and they are together advanced through the vessel to the region of interest without using an initial guidewire. In this embodiment the catheter/filter combination will be used to navigate through the vessel to the region of interest. Then the catheter is withdrawn to deploy the filter. In a second alternative, an introduction guidewire is advanced to the region of interest, and the filter (contained in a catheter) is advanced over the guidewire to the region of interest, at which point the catheter is removed leaving the deployed filter near the region of interest on the guidewire. In this embodiment the filter is not comprised of an elongate support member as previously defined, and the guidewire and/or filter may be configured to preserve a spatial relationship between the guidewire and the filter. For example, the guidewire may be configured to prevent the filter from advancing beyond the distal end of the guidewire.

In other embodiments of the invention, no catheter is required for filter delivery. For example, the filter may be stretched axially so as to reduce its diameter to a size suitable for navigation through a vessel and across a treatment site.

Typical dimensions of a filter used in the devices of this invention range from 2 mm to 90 mm in length, and from about 0.5 mm to 2 mm in diameter before deployment, and from about 2 mm to 30 mm in diameter after deployment. A typical guidewire is about 0.2 to 1.0 mm in diameter and ranges from 50 cm to 320 cm in length.

The components of the distal protection system are made from biocompatible materials. Materials also may be surface treated to produce biocompatibility. The elongate support member may be formed of any material of suitable dimension, and preferably comprises metal wire. Suitable materials include stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, and the like. A shape memory or superelastic metal such as nitinol is also suitable. The elongate support member may be solid or may be hollow over some or all of its length.

The material used to make the filter or filter support structure is preferably self-expanding. Suitable materials include metals such as stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, silk, and the like. A shape memory or superelastic metal is particularly suitable for those applications when it is desired for an element, such as a filter, to assume a pre-determined three-dimensional shape or for a guidewire to maintain a pre-determined curvature. A shape memory or superelastic metal comprising nickel and titanium known as "nitinol" is commercially available in various dimensions and is suitable for use as both a guidewire and a filter. For example, nitinol tubular braid can be heat set into a desired shape, compressed for delivery to a site, and then released to resume the heat-set shape.

The filter element has a body defining an interior cavity. The filter body has a plurality of openings or pores such that, when the filter element is in its deployed configuration within the vessel lumen, fluid flows through the filter element and particles of the desired size are captured inside the interior cavity of the filter element.

The filter may comprise any material that is suitably flexible and resilient, such as a mesh, i.e., a material having openings or pores. The filter may comprise braided, knitted, woven, or non-woven fabrics that are capable of filtering particles, preferably having pore sizes from 30 to 500 microns. Woven or non-woven fabrics may additionally be treated to fuse some or all of the fiber intersections. The fabric may be spun or electrospun. Suitable materials include those formed from sheets, films, or sponges, polymeric or metallic, with holes formed by mechanical means such as laser drilling and punching, or by chemical means such as selective dissolution of one or more components. For example, a suitable filter material is braided tubular fabric comprising superelastic nitinol metal. Mesh fabric of nitinol material can be heat-set to a desired shape in its expanded configuration.

The material comprising the filter is preferably at least partially radiopaque. This material can be made radiopaque by plating, or by using core wires, tracer wires, or fillers that have good X-ray absorption characteristics compared to the human body. Radiopaque filters are described in U.S. patent application Ser. No. 10/165,803, filed Jun. 7, 2002, entitled "Radiopaque Distal Embolic Protection Device," the contents of which are hereby incorporated by reference herein.

The embodiments of this invention, described in detail below in connection with the figures, are suitable for use with various distal protection systems that are known in the art. The filter may have a windsock type shape. The construction, deployment and retrieval of a filter having this shape is described, for example, in U.S. Pat. No. 6,325,815 B1 (Kusleika et al.), the contents of which are hereby incorporated by reference herein.

The filter may also be a cup-shaped or basket-shaped device which forms a proximally facing opening when expanded. The construction, deployment, and retrieval of such a filter is described in WO 96/01591 (Mazzocchi et al.). This cup-shaped device may generally resemble an umbrella or a parachute, having a dome-like structure curving radially outwardly from the guidewire or elongate support member. Other shapes may be equally suitable in performing a filtering function, such as a conical shape, or a relatively flat disc shape. It will be appreciated that the shape of these filtration devices shown in various embodiments are merely illustrative and are not meant to limit the scope of the invention.

Regardless of the shape of the filter, the filter preferably is deployed using an elongate support member. This can be done in various ways, and one or both of the proximal and distal ends of the filter may be affixed to the elongate support member (by a fixed element) or may be slidably disposed about the elongate support member (by one or more sliding elements).

One type of sliding element comprises inner and outer annular rings. The first ring fits within the second ring. The inner diameter of the first ring is larger than the diameter of the elongate support member so that the sliding element can slide over the elongate support member. The sliding element can be affixed to the filter fabric by placing the fabric between the first and second rings. However, this is not meant to be limiting, and the filter fabric can also be affixed to the sliding element by adhesive, solder, crimping, or other means known in the art. The sliding element may comprise any stiff material such as metal or polymer and preferably the slider is radiopaque. Suitable materials include stainless steel, titanium, platinum, platinum/iridium alloy, gold alloy, polyimide, polyester, polyetheretherketone (PEEK), and the like. Movement of a sliding element with respect to the elongate support member can be facilitated by coating one or both of the inside of the sliding element and the outside of the elongate support member with a friction-reducing coating, such as polytetrafluoroethylene or a lubricious hydrophilic coating.

Fixed elements include annular rings. Also included within this meaning is an element that is crimped, adhered, soldered, or otherwise fastened directly to the elongate support member. Also, the filter fabric may be attached directly to the elongate support member. In any event, the sliding and fixed elements (or any attachment point) typically comprise radiopaque material to assist in the placement of the filter. In addition, one or more radiopaque markers may be positioned at various locations on the protection device. These radiopaque markers or marker bands comprise a material that will be visible to X-rays and they assist in positioning the device.

Some distal protection filters include a floppy tip at a distal portion of the guidewire or elongate support element. The floppy tip provides an atraumatic and radiopaque terminus for the device. An atraumatic tip prevents vessel injury during initial placement or subsequent advancement of the device. A radiopaque tip helps the physician verify suitable tip placement during fluoroscopy. The floppy tip preferably comprises a springy or resilient material, such as a metal (e.g., stainless steel, iron alloys such as Elgiloy™, platinum, gold, tungsten, and shape memory or superelastic metal such as nitinol) or polymer (e.g., polyetheretherketone (PEEK), polyimide, polyester, polytetrafluoroethylene (PTFE), and the like). Springy materials are desirable because they tend to retain their shape. The physician will initially shape the tip, typically with a slight curve, and then as the device is advanced through the body the tip will be deflected as it encounters obstacles. It is desirable, after the inevitable deflections during insertion, that the tip restore itself to the pre-set shape. Polymeric materials additionally may be reinforced with metals or other fillers. The tip may be a monofilament or multifilament (such as a cable). The floppy tip may be tapered or have a uniform diameter over its length. The floppy tip may comprise a tube, or could have circular, flat, or other cross-sections. It may be coiled. The tip may comprise one or more elements (for example, parallel independent structures). The tip may be polymer-coated or otherwise treated to make the surface slippery. The floppy tip can be any desired length.

The filter comprises biocompatible materials such as metals and polymeric materials. Materials such as metals and polymeric materials can be treated to impart biocompatibility by various surface treatments, as known in the art. When wire is used, the wire is selected on the basis of the characteristic desired, i.e., stiffness or flexibility, and the properties can depend upon both the diameter of the wire and its cross-sectional shape. The size, thickness, and composition of elastic materials are selected for their ability to perform as desired as well as their biocompatibility. It is to be understood that these design elements are known to one of skill in the art.

Filters are typically constructed as described in U.S. Pat. No. 6,325,815 B1. See column 3, line 63, to column 4, line 16; and column 4, line 48, to column 5, line 36. The filter body typically comprises a length of a braided tubular fabric, preferably made of nitinol. The filter body is typically made by placing a braided tubular fabric in contact with a molding surface of a molding element which defines the shape of the desired filter body. By heat treating the braided tubular fabric in contact with the molding surface of the molding element, one can create a filter body having virtually any desired shape.

Braiding is a process for producing a tubular interwoven structure from individual strands. Braids are typically produced in continuous lengths on commercially available braiding machines. Some commercial products produced on braiding machines include rope, shoelaces, and reinforcing jackets for electrical cable. Medical products produced by braiding include stents, vascular grafts, and catheter reinforcing layers.

In a typical braiding process for making a 72 stranded braid, lengths of strands, such as wire, are wound onto bobbins. In this example 72 bobbins are wound with wire. Each bobbin is loaded into the carrier of a 72 carrier braiding machine. Typically braiding machines for medical use have from 16 to 144 carriers or more. Each wire is led through a tensioning mechanism in the carrier and all wire strands are gathered at a common central elevated position along the (typically vertical) axis of the braiding machine, where they are fastened to a take-up mechanism. The take-up mechanism may be a long mandrel arranged along the axis of the braiding machine and onto which the braid is formed during the braiding process. Once so configured, the carriers are rotated relative to the axis of the braiding machine. The carriers are rotated in a serpentine path, half of them moving clockwise and the other half moving counterclockwise, so as to interweave the strands in a programmed pattern. While the carriers are rotating, the take-up mechanism advances the woven braid in a direction away from the carriers. The combination of these motions produces a helix of strands twisting in a clockwise direction along the mandrel, interwoven with a helix of strands twisting in a counterclockwise direction along the mandrel. In this manner continuous lengths of braid are produced with an inside diameter of the braid equal to the outside diameter of the braiding mandrel. The individual braid strands, while still on the mandrel, can be twisted together after the length of the mandrel has been braided. If desired, after removing the mandrel from the braiding machine, the strands can be heat-treated. In the case of nitinol strands, heat treatment on the mandrel at about 525° C. for 10 minutes or so can cause the nitinol-braided fabric to remember the shape and size of the mandrel when the nitinol is at rest.

The average pore sizes of filters of the invention preferably range from 30 to 300 microns. In another preferred embodiment, the average pore sizes range from 30 to 150 microns. A pore size of about 120 microns is preferred for devices intended to be used in connection with coronary procedures and a pore size of about 50 microns is preferred for devices intended to be used in connection with carotid or intracranial procedures. The variation in pore size within the filter should be minimized. In preferred embodiments of the invention, the standard deviation of the pore size is less than 20 percent of the average pore size. In other preferred embodiments, the standard deviation of the pore size is less than 15, 10, 5, or 2 percent of the average pore size.

The percent open area of the filters of the invention is preferably greater than 50 percent. In other preferred embodiments, the percent open area is greater than 60, 70, or 80 percent. A standard formula is used to calculate the percent open area of a given design. The percent open area is calculated by dividing the total pore area by the total filter area (including the pore area).

The filters of the invention preferably are made of a material having a tensile strength of greater than 70,000 psi (7031 kg/cm$^2$), more preferably greater than 150,000 psi (14,062 kg/cm$^2$), and more preferably greater than 200,000 psi (17,578 kg/cm$^2$). Cast polymer films have a maximum tensile strength of about 10,000 psi (703 kg/cm$^2$); oriented polymer films have a tensile strength as high as 50,000 psi (3516 kg/cm²), and metal filters typically contain wires having a tensile strength of from 70,000 to 300,000 psi (7031 kg/cm² to 21,093 kg/cm²).

The various embodiments of the invention will now be described in connection with the drawing figures. It should be understood that for purposes of better describing the invention, the drawings have not been made to scale. Further, some of the figures include enlarged or distorted portions for the purpose of showing features that would not otherwise be apparent. The material comprising the filter (e.g., mesh or fabric with pores, as described above) is omitted in the figures for simplicity.

It is to be understood that the following embodiments are useful for any shape or type of filter. For example, these embodiments are useful for any filter deliverable by any manner to a desired position in a body lumen where control of the desired characteristics of the filter as set forth above is desired. In particular, the invention includes both proximal and distal filters.

Figure 1A:
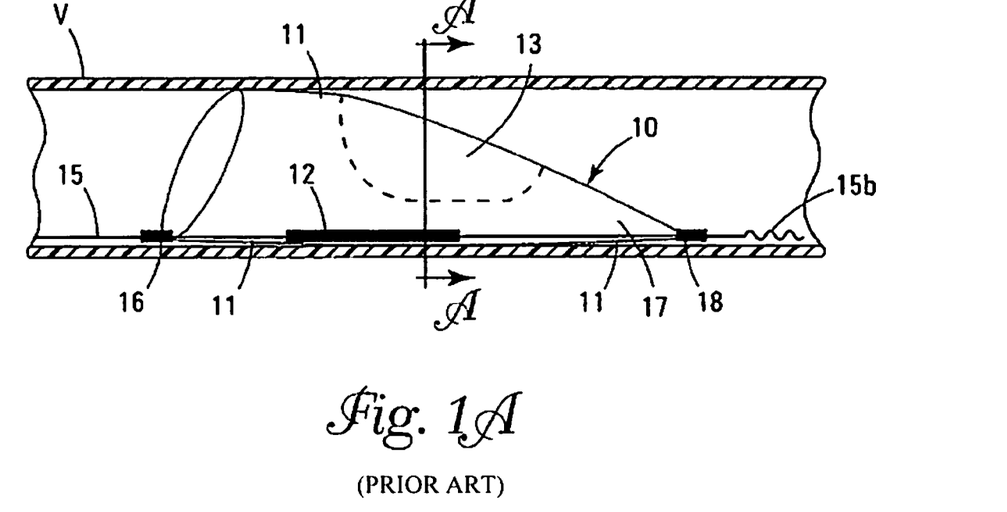
FIG. 1A is a side view and FIG. 1B is a cross sectional view of a prior art filter deployed in a body conduit.

FIG. 1A illustrates a prior art distal protection system in which windsock-shaped filter 10 is attached to elongate support member 15 via distal sliding element 18. For clarity, the mesh of the filter is not drawn in the figure. At the proximal end of the filter, proximal sliding element 16 is slidably disposed about the elongate support member and attached to filter 10. Stop 12 is provided on the elongate support member in order to limit the relative motion of the filter along the support member. Support member 15 terminates distally at floppy tip 15b.

Figure 1B:
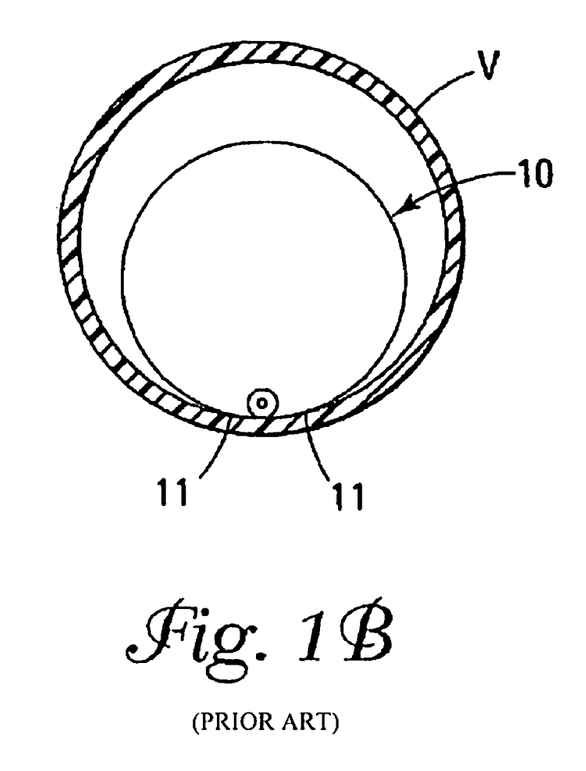

When deployed in a vessel V, filter 10 has wall apposition regions 11 at the proximal end of the filter and along the vessel wall. FIG. 1B shows filter 10 and wall apposition regions 11 in cross section. Fluid flow cannot pass through filter 10 in wall apposition regions 11 because there is no space between the filter and the vessel in this region. In the case of a braided structure, flow cannot pass through distal portion of mesh 17 because the pores are generally very small. Most flow is confined to passing through the central portion 13 of filter 10.

Distal Loop Filters

Figure 2A:
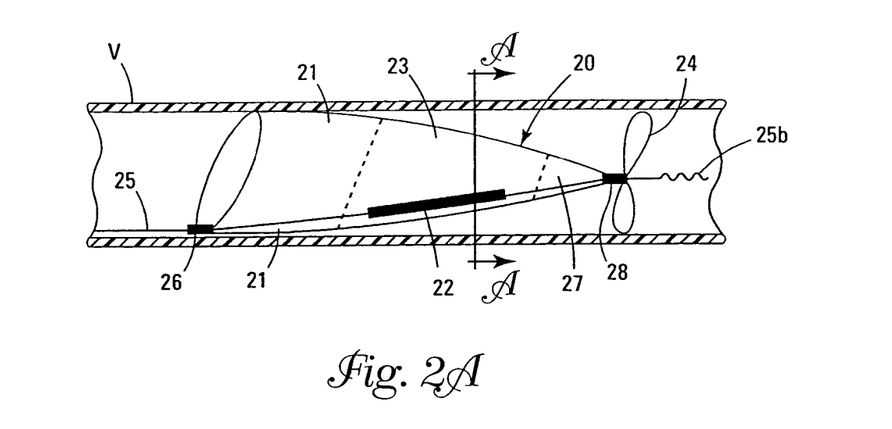
FIG. 2A is a side view and FIG. 2B is a cross sectional view of an embodiment of the invention showing a distal loop.
Figure 2B:
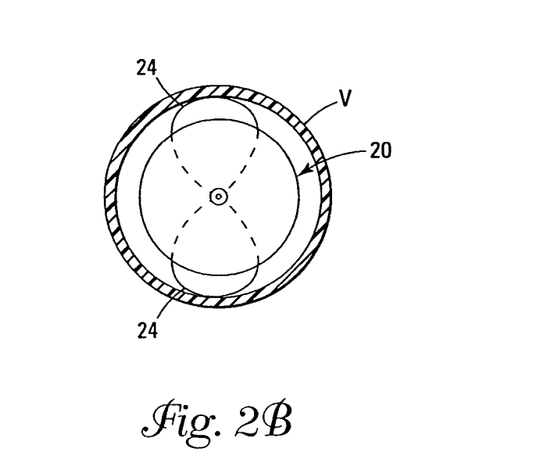

FIG. 2A is a side view and FIG. 2B is a cross sectional view of an embodiment of the present invention. Windsock-shaped filter 20 is attached to elongate support member 25 via distal sliding element 28. For clarity, the mesh of the filter is not drawn in the figure. At the proximal end of the filter, proximal sliding element 26 is slidably disposed about the elongate support member and attached to filter 20. Stop 22 is provided on the elongate support member in order to limit the relative motion of the filter along the support member. Stop 22 may be a wire coil or a hypotube, polymer or metal, solid, or cut to improve its flexibility. Stops and the use of stops are described in U.S. Ser. No. 10/060,271, filed Jan. 30, 2002, entitled "Slidable Vascular Filter," the contents of which are hereby incorporated by reference herein. Support member 25 terminates distally at floppy tip 25b. Distal loop 24 attaches to distal sliding element 28 and contacts vessel wall. Distal loop 24 may be made of elastic material such as metal or polymer and biased to expand when unconstrained. Suitable materials include nitinol, stainless steel, ELGILOY™, polyimide, PEEK, liquid crystal polymer, polyester, and the like. If made of nitinol, the distal loop can be heat set to the desired expanded shape for example by heating to 525° C. for about two minutes. When deployed in a vessel V, filter 20 has wall apposition regions 21 at the proximal end of the filter but not along the vessel wall distal of the proximal end. FIG. 2B shows filter 20 in cross section, where it is apparent that wall apposition regions are not present as they are in FIG. 1B. In the case of a braided structure, flow cannot pass through distal portion of mesh 27 because the pores are generally very small. Most flow is confined to passing through the central portion 23 of filter 20, and this central portion 23 of filter 20 is enlarged compared to prior art filters due to the effect of distal loop 24.

In FIG. 2, due to the effects of the distal loop, the wall apposition region of the filter is reduced compared to prior art filters. However, the radial motion of the elongate support member 25 wire can compromise the necessary wall apposition of the proximal end of filter.

Figure 3:
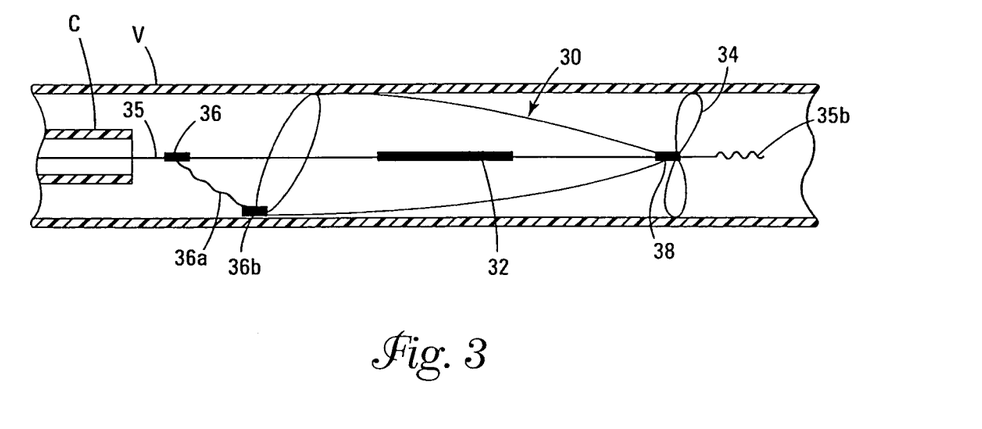
FIG. 3 is a side view of an embodiment of the invention showing a distal loop and a tether.

FIG. 3 illustrates a windsock-shaped filter 30 attached to elongate support member 35 via distal sliding element 38. For clarity, the mesh of the filter is not drawn in the figure. At the proximal end of the filter, proximal sliding element 36 is slidably disposed about the elongate support member and attached via tether 36a to point 36b on the filter 30. Stop 32 is provided on the elongate support member in order to limit the relative motion of the filter along the support member. Stop 32 may be a wire coil or a hypotube, polymer or metal, solid, or cut to improve its flexibility. Support member 35 terminates distally at floppy tip 35b. Distal loop 34 attaches to distal sliding element 38 and contacts the vessel wall. Distal loop 34 can attach to the proximal end, distal end, or at any point along distal sliding element 38, and is configured so as to collapse into a catheter of low profile by incorporating hinges, zones of preferential bending, and the like.

Tether 36a reduces the influence of radial wire motion on the filter mouth. Tether 36a may be made of any strong biocompatible flexible strand. Suitable materials include metal, polymer, monofilament, stranded, or cabled. For example, 0.004 inch (0.10 mm) diameter nitinol stranded wire made of 7 strands can be used. More preferably, 0.004 inch (0.10 mm) diameter 49 stranded nitinol cable can be used. Stranded wire generally has more flexibility than monofilament wire of the same overall diameter, and cabled wire generally has more flexibility than stranded wire of the same overall diameter. Other suitable materials include KEVLAR™ fiber, DACRON™ fiber, and other textile fibers. Stainless steel wires, particularly in stranded or cabled form, may be preferred in some embodiments due to their high strength. Further, it is desirable to coat the tethers with thrombosis reducing materials such as heparin to reduce clot formation on the tether.

By positioning elongate support member 35 such that there is slack in tether 36a, the elongate support member can move laterally within the filter without compromising filter wall apposition. Tethers are more effective at accommodating lateral elongate member motion as compared to the struts commonly used in prior art designs. It is also expected that proximal sliding element 36 will slide to relieve tether tension in the event of lateral or radial elongate member motion, thereby preventing loss of filter apposition to a vessel wall. Struts, common in prior art designs, do not afford this degree of freedom for accommodating elongate member motion. In addition, by locating elongate member 35 within filter 30, lateral motion of the elongate member will tend to press filter 30 against the vessel wall because the filter wall is between the vessel and the elongate member. Further, good wall apposition of a given filter size is expected over a range of vessel diameters because there is no stiff hoop at the opening of filter 30, rather, the filter mesh is gathered at connection 36b. In contrast, many prior art designs have a stiff hoop at the proximal end of the filter and such designs have difficulty accommodating a range of vessel diameters due to the difficulty in collapsing the stiff hoop while maintaining close contact with the vessel wall.

This device can be deployed and used as follows. The proximal end of elongate member 35 is inserted into the distal end of catheter C (back loaded into catheter). Elongate member 35 is withdrawn proximally through catheter C causing stop 32 to contact slider 36, causing tension to be applied to tether 36a and resulting in filter 30 being drawn into catheter C due to attachment of tether 36a to filter 30 at point 36b. Further proximal motion of the elongate member through catheter C draws the rest of filter 30, distal loop 34, and optionally floppy tip 35b into catheter. The catheter with filter assembly therein is advanced to a region of interest and deployed nearby, generally distal of the region of treatment in the embodiment shown in FIG. 3. Filter deployment is accomplished by advancing filter 30 distally relative to catheter C. In a preferred embodiment, filter 30 in catheter C is positioned distal to a treatment site, and catheter C is withdrawn proximally. Filter 30 will remain inside catheter C due to friction of filter against catheter walls until distal sliding element 38 contacts stop 32. Catheter C will then slide relative to filter 30, with reduced friction due to the tendency of filter 30 to elongate and reduce in diameter due to action of stop 32 on distal sliding element 38. As catheter C is withdrawn proximally relative to filter 30, first distal loop 34, then filter 30 will exit the catheter and expand to contact the vessel wall. Catheter C can then be withdrawn proximally and removed from the patient. At this point, treatment and diagnostic catheters can be introduced over elongate member 35. Excessive motion of filter 30 against the wall of vessel V during catheter exchanges is prevented because sliders 36, 38 allow axial and rotational motion between elongate member 35 and filter 30. During treatment or diagnosis, emboli may be released from the treated or diagnosed site and may be collected in the filter.

Alternatively, filter 30 can be front loaded into catheter C by introducing floppy tip 35b into the proximal end of catheter C and pushing elongate member 35 distally. Stop 32 will push against distal sliding element 38 and cause distal loop 34, filter 30, tether 36a, and proximal sliding element 36 to enter into catheter C and advance distally through catheter C. In this alternative, catheter C can be advanced to a region of interest with the filter contained within. More preferably, a guidewire can be advanced to a region of interest, catheter C advanced to the region of interest over the guidewire, the guidewire withdrawn from catheter C, and filter 30 front loaded to the region of interest and deployed as described above.

To recover the filter, catheter C is advanced over elongate support member 35 and the elongate support member is withdrawn into catheter C. Stop 32 will abut proximal slider 36, and slider 36 coupled to tether 36a coupled to filter 30 by way of point 36b will cause filter 30 to be recovered into catheter C by continued proximal motion of elongate support member 35 relative to catheter C. Support member 35 preferably should be withdrawn sufficiently to at least close the opening of filter 30; alternatively all or part of filter 30 and distal loop 34 may be withdrawn into catheter C. It is preferable to draw the distal loop at least partially into catheter C so as to reduce or eliminate contact of distal loop with the vessel wall. At this time, the filter/catheter combination can be withdrawn from the patient.

Figure 4:
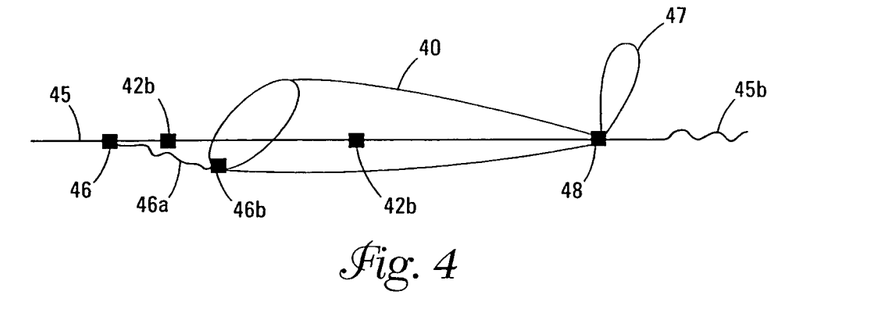
FIG. 4 is a side view of an alternate embodiment of a filter of this invention.

FIG. 4 illustrates an alternative embodiment of a filter of this invention in which windsock-shaped filter 40 is attached to elongate support member 45 via distal sliding element 48. At the proximal end of the filter, proximal sliding element 46 is slidably disposed about the elongate support member and attached via tether 46a to point 46b on the filter. Point 46b can be constructed in a manner similar to that for sliders 46, 48, or can be a structure such as a tube into which tether 46a and filter 30 are inserted and held together by crimping the tube, joining with adhesive, welding, or the like. Stops 42a and 42b are provided on the elongate support member in order to limit the relative motion of the filter along the support member. Stop 42a is shown proximal to the filter opening and stop 42b is shown within the filter. Alternatively one stop, such as a wire coil or a hypotube, polymer or metal, solid or cut to improve its flexibility, can take the place of stops 42a and 42b. Support member 45 terminates distally at floppy tip 45b. Distal loop 47 is affixed to distal sliding element 48. The distal loop serves to keep the filter open during movement of the elongate support member relative to the filter and to prevent the elongate support member 45 from moving radially and collapsing filter 30. This is accomplished by keeping the elongate support member, which slides through the distal sliding element 48, opposed to a vessel wall. A further advantage of distal loop stabilization of wire position is that the distal loop does not impede entry of embolic particles into the filter, unlike prior art approaches where struts and the like are often placed proximal to the filter. Another advantage of a distal loop filter is that the mass of the loop and the comparatively large mass of the proximal filter do not overlap during collapse of these structures into a delivery catheter, and as a result the profile of a delivery catheter for the filter can be made smaller. Filter 40 can comprise metal or polymer braid, polymer film with holes drilled therethrough, foams, other filter media as is known in the art, or any of the filter mesh structures disclosed in the U.S. patent applications filed on the same date as the present application and entitled "Embolic Filters With Controlled Pore Size" Ser. No. 10/354,679 and "Embolic Filters Having Multiple Layers and Controlled Pore Size" Ser. No. 10/354,829, the contents of each of which are hereby incorporated by reference herein.

No Loop Filters

Figure 5:
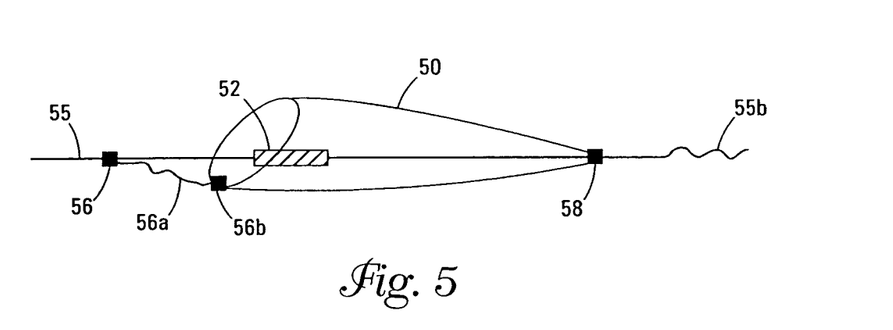
FIG. 5 is a side view of a no loop filter.

FIG. 5 illustrates a distal protection system similar to that shown in FIG. 4, but without the distal loop. Windsock-shaped filter 50 is attached to elongate support member 55 via distal sliding element 58. At the proximal end of the filter, proximal sliding element 56 is slidably disposed about the elongate support member and attached via tether 56a to point 56b on the filter. Stop 52 is provided on the elongate support member between the distal and proximal elements. The stop limits the relative motion of the filter along the support member. Support member 55 terminates distally at floppy tip 55b which may comprise a coil tip or any of the embodiments described earlier. Filter 50 is comprised of any of the filter mesh structures disclosed herein. An advantage of a filter with no distal loop is that the mass of the filter assembly is reduced, and as a result the profile of a delivery catheter for the filter can be smaller. Further, no loop filters have fewer stiff structures associated with the distal end of the filter. These attributes allow no loop filters to cross tighter lesions and to track more easily through tortuous vessels.

Figure 6:
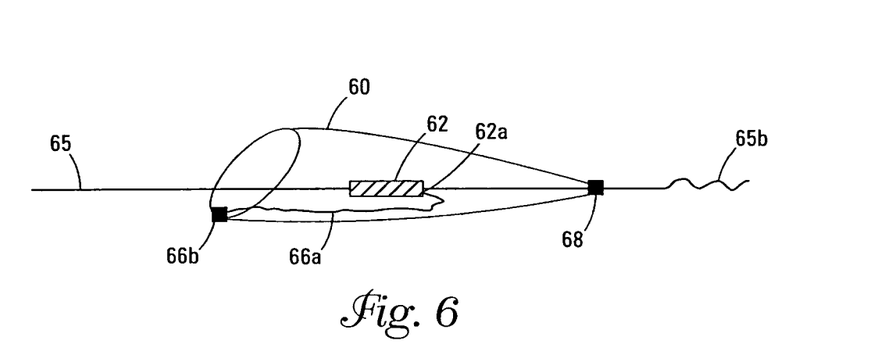
FIG. 6 is a side view of an alternate embodiment of a no loop filter.

FIG. 6 illustrates a variation of the distal embolic protection system shown in FIG. 5. Filter 60 is disposed about elongate support member 65 via distal sliding element 68 and is comprised of any of the filter mesh structures disclosed herein. Stop 62 is provided on the support member and tether 66a is attached to the distal end of the stop (at point 62a) and the proximal end of the filter (at point 66b), although the tether could be attached to either end of the stop or at any point therealong. The stop/tether structure limits the relative motion of the filter along the support member and provides for radial motion of the elongate support member. Support member 65 terminates distally at floppy tip 65b.

Although we have generally used siding elements to describe the invention, one or more fixed element could take the place of the sliding elements.

While the examples given generally relate to distal embolic protection filters it is envisioned that the invention can apply to proximal filters as well.

While the examples given generally relate to windsock shaped filters it is envisioned that the invention can apply to filters of nearly any shape including cups, plates, cylinders, ovoids, and others. Generally, the invention is best embodied in filters having an opening facing towards the direction of flow so that emboli have a tendency to enter the filter.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A device for filtering emboli from blood flowing through a lumen defined by walls of a vessel in a patient's body, comprising:
   an elongate support member;
   a filter element carried on and attached to the elongate support member, the filter element being expandable from a collapsed configuration when the filter element is restrained to an expanded configuration when the filter element is unrestrained, wherein the filter element comprises a self-expanding filter mesh material having pores, wherein the filter element has proximal and distal portions and a central portion, the filter element having a shape in the expanded configuration which defines a cavity having a proximal facing opening; and
   a self-expanding radial element associated with the filter element, wherein the self-expanding radial element is distal of the filter element, and the self-expanding radial element is adapted to maintain the filter element centered in the lumen, the filter element being attached to the self-expanding radial element by a sliding element positioned between the filter element and the self-expanding radial element, the sliding element being slidable in relation to the elongate support member.

2. A device of claim 1, wherein the self-expanding radial element comprises a loop, and wherein the loop is generally circular in shape.

3. A device of claim 2, wherein the self-expanding radial element has one loop.

4. A device of claim 2, wherein the self-expanding radial element comprises two or more loops.

5. A device of claim 4, wherein the self-expanding radial element has two loops.

6. A device of claim 1, wherein the filter element is attached to the elongate support member at the distal portion of the filter element.

7. A device of claim 6, wherein the elongate support member is attached to the filter element at the proximal portion of the filter element.

8. A device of claim 1, wherein the self-expanding radial element is adapted to not significantly impede the flow of blood through the lumen.

9. A device of claim 1, wherein the device does not comprise any other self-expanding elements other than the self-expanding filter mesh material having pores and the self-expanding radial element.

10. A device of claim 1, wherein the self-expanding radial element is made of nitinol wire.

11. A device of claim 1, wherein when the self-expanding radial element is in its expanded configuration, the self-expanding radial element generally defines a plane substantially perpendicular to the elongate support member.

12. A device of claim 1, wherein when the filter element is in the expanded configuration, the average pore size is from 30 to 300 microns and the standard deviation of the pore size is less than 20 percent of the average pore size.

13. A device of claim 1, wherein when the filter element is in the expanded configuration, the filter element has a percent open area greater than 50 percent.

14. A device of claim 1, wherein when the filter element is in the expanded configuration, the filter element has a percent open area greater than 60 percent.

15. A device of claim 1, wherein when the filter element is in the expanded configuration, the filter element has a percent open area greater than 70 percent.

16. A device of claim 1, wherein when the filter element is in the expanded configuration, the filter element has a percent open area greater than 80 percent.

17. A device of claim 1, wherein the self-expanding filter mesh material has a tensile strength greater than 70,000 psi.

18. A device of claim 1, wherein the self-expanding filter mesh material has a tensile strength greater than 100,000 psi.

19. A device of claim 1, wherein the self-expanding filter mesh material has a tensile strength greater than 200,000 psi.

20. A device of claim 1, wherein the self-expanding filter mesh material is made of metal.

21. A device of claim 1, wherein the self-expanding filter mesh material is made of nitinol.

22. A device of claim 1, wherein the self-expanding filter mesh material comprises wires braided to form diamond-shaped pores.

* * * * *